US008377436B2

(12) United States Patent
Chen et al.

(10) Patent No.: US 8,377,436 B2
(45) Date of Patent: Feb. 19, 2013

(54) GRANULYSIN AND USES THEREOF

(75) Inventors: Yuan-Tsong Chen, Taipei (TW); Wen-Hung Chung, Nantou (TW); Shuen-Iu Hung, Chang-Hwa (TW)

(73) Assignees: Academia Sinica, Taipei (TW); Chang Gung Medical Foundation, Linkou Branch, Taoyuan Hsien (TW)

( * ) Notice: Subject to any disclaimer, the term of this patent is extended or adjusted under 35 U.S.C. 154(b) by 45 days.

(21) Appl. No.: 12/764,260

(22) Filed: Apr. 21, 2010

(65) Prior Publication Data

US 2011/0014215 A1 Jan. 20, 2011

Related U.S. Application Data

(62) Division of application No. 11/767,120, filed on Jun. 22, 2007, now Pat. No. 7,718,378.

(60) Provisional application No. 60/805,614, filed on Jun. 23, 2006.

(51) Int. Cl.
*A61K 39/00* (2006.01)
*A61K 39/395* (2006.01)

(52) U.S. Cl. ................ 424/130.1; 424/139.1; 424/141.1

(58) Field of Classification Search ........................ None
See application file for complete search history.

(56) References Cited

PUBLICATIONS

Krensky et al. 'Biology and clinical relevance of granulysin.' Tissue antigens. 73:193-198, 2009.*

Zitvogel et al. 'The multifacted granulysin.' Bood. 116(18):3379-3380, 2010.*

Akhtar et al. 'Nonviral delivery of synthetic siRNAs in vivo.' The Journal of Clinical Investigation 117(12):3623-3632, 2007.*

Alakulpi, Noora S., et al, "Diagnosis of Acute Renal Allograft Rejection by Analyzing Whole Blood mRNA Expression of Lymphocyte Marker Molecules", *Transplantation*, vol. 83, No. 6, Mar. 27 2007; 791-79.8.

Nagasawa, Masayuki, et al, "Analysis of Serum Granulysin in Patients with Hematopoietic Stem-Cell Transplantation: Its Usefulness as a Marker of Graft-Versus-Host Reaction", *American Journal of Hematology* 81:340-348 (2006).

Kotsch, Katja, et al, "Enhanced Granulysin mRNA Expression in Urinary Sediment in Early and Delayed Acute Renal Allograft Rejection", vol. 77, 1866-1875, No. 12, Jun. 27, 2004 *Transplantation*.

Ogawa et al., "Granulysin in Human Serum as a Marker of Cell-Mediated Immunity," Eur. J. Immunol. 33:1925-1933 (2003).

Clayberger et al., "Granulysin," Curr. Opin. Immunol. 15:560-565 (2003).

Chung et al., "Granulysin is a Key Mediator for Disseminated Keratinocyte Death in Stevens-Johnson Syndrome and Toxic Epidermal Necrolysis," Nature Med. 14(12):1343-1350 (2008).

Sarwal et al., "Granulysin Expression ins a Market for Acute Rejection and Steriod Resistance in Human Renal Transplantation," Human Immunology, 62:21-31 (2001).

* cited by examiner

*Primary Examiner* — Nora Rooney

(74) *Attorney, Agent, or Firm* — Occhiuti Rohlicek & Tsao LLP

(57) ABSTRACT

Disclosed are uses of granulysin in methods of diagnosing or treating autoimmune disorders.

5 Claims, No Drawings

GRANULYSIN AND USES THEREOF

RELATED APPLICATION

This application is a divisional of U.S. application Ser. No. 11/767,120, filed on Jun. 22, 2007, which claims priority to U.S. Provisional Application Ser. No. 60/805,614, filed Jun. 23, 2006. The contents of these applications are incorporated herein by reference in their entirety.

BACKGROUND

Unwanted immune responses are involved in various disorders. Examples of these disorders include adverse drug reactions (ADRs), graft-versus-host diseases (GVHD), inflammatory diseases, autoimmune diseases, transplant rejection, allergic diseases, and T cell-derived cancers. All of them are major clinical problems.

For example, ADRs account for 6-7% of all hospital admissions and remain. Stevens-Johnson syndrome (SJS) and toxic epidermal necrolysis (TEN) are life-threatening cutaneous ADRs characterized by massive keratinocyte apoptosis. These two disorders are considered to be variants of the same disease with different severity as both are characterized by a rapidly developing blistering exanthema of purpuric macules and target-like lesions accompanied by mucosal involvement and skin detachment to a varying extent (Roujeau et al., N. Engl. J. Med. 1994 Nov. 10; 331(19):1272-85). SJS is defined as skin detachment of less than 10%, TEN as greater than 30%, and overlapping SJS/TEN as 10-30% (Roujeau et al., J. Invest. Dermatol. 1994 June; 102(6):285-305). The histopathology observations of SJS and TEN include marked keratinocyte apoptosis in the epidermis with dermo-epidermal separation and epidermal necrosis, resulting in bullae and extensive mucocutaneous shedding Paul et al. Br. J. Dermatol. 1996 April; 134(4):710-4. Besides the severe cutaneous manifestations, SJS/TEN may be accompanied by fever, myocarditis, myocardial infarction, hepatitis, acute renal failure, and affect respiratory and gastrointestinal systems. Although the incidence of SJS/TEN is low, these conditions can kill or severely disable previously otherwise healthy people. A few cases have prompted the pharmaceutical companies' withdrawal of newly released drugs (Roujeau et al., N. Engl. J. Med. 1994 Nov. 10; 331(19):1272-85).

There is a need for methods to diagnose or treat diseases associated with unwanted immunological responses.

SUMMARY

This invention relates to use of granulysin in diagnosing and treating diseases associated with unwanted immunological responses, such as cytotoxic T cell-mediated disorders, granulysin-mediated autoimmune disorders, and autoimmune disorders.

In one aspect, the invention features a method of diagnosing one or more of the just-mentioned disorders, such as a granulysin-mediated autoimmune disorder, in a subject. The method includes obtaining a test sample from a subject; determining an expression level of granulysin in the test sample; and comparing the expression level to a predetermined value. The subject is determined to have or to be at risk of having the disorder if the expression level is higher than the predetermined value. The disorder can be Stevens-Johnson syndrome, toxic epidermal necrolysis, graft-versus-host disease, Behcet disease, ankylosing spondylitis, systemic lupus erythematosus, dermatomyositis, polymyositis, and rejection disorder of organ transplantation. The test sample can be a bodily fluid sample, such as a blister fluid sample or a serum sample. In one example, the granulysin includes the sequence of the 9 KDa form (SEQ ID NO: 1), the 15 KDa form (SEQ ID NO: 3) or an antigenic fragment of them. List below are the amino acid sequences (SEQ ID NOs: 1 and 3) and the nucleotide sequences encoding the polypeptides (SEQ ID NOs: 2 and 4). The segment lacking in the 9 KDa form is underlined (SEQ ID NO: 5). The fragment is at least 10 (e.g., 11, 15, 18, 20, 30, 50, or 100,) amino acid residues in length. In one example, the fragment contains SEQ ID NO: 5 or its fragment.

SEQ ID NO 1:
GRDYRTCLTIVQKLKKMVDKPTQRSVSNAATRVCRTGRSRWRDVCRNF
MRRYQSRVTQGLVAGETAQQICEDLRLCIPSTGPL

SEQ ID NO 2:
ggccgtgactacaggacctgtctgacgatagtccaaaaactgaagaag
atggtggataagcccacccagagaagtgtttccaatgctgcgacccgg
gtgtgtaggacggggaggtcacgatggcgcgacgtctgcagaaatttc
atgaggaggtatcagtctagagttacccagggcctcgtggccggagaa
actgcccagcagatctgtgaggacctcaggttgtgtataccttctaca
ggtcccctctga SEQ ID NO 3:
MATWALLLLAAMLLGNPGLVFSRLSPEYYDLARAHLRDEEKSCPCLAQ
EGPQGDLLTKTQELGRDYRTCLTIVQKLKKMVDKPTQRSVSNAATRVC
RTGRSRWRDVCRNFMRRYQSRVTQGLVAGETAQQICEDLRLCIPSTGP
L SEQ ID NO 4:
atggctacctgggccctcctgctccttgcagccatgctcctgggcaac
ccaggtctggtcttctctcgtctgagccctgagtactacgacctggca
agagcccacctgcgtgatgaggagaaatcctgcccgtgcctggcccag
gagggcccccagggtgacctgttgaccaaaacacaggagctgggccgt
gactacaggacctgtctgacgatagtccaaaaactgaagaagatggtg
gataagcccacccagagaagtgtttccaatgctgcgacccgggtgtgt
aggacggggaggtcacgatggcgcgacgtctgcagaaatttcatgagg
aggtatcagtctagagttacccagggcctcgtggccggagaaactgcc
cagcagatctgtgaggacctcaggttgtgtataccttctacaggtccc
ctctga The invention also features a method of monitoring the progression of one or more of the above-mentioned disorders in a subject. The method includes determining an expression level of granulysin in a test sample from the subject. The invention further features a method of evaluating a subject who is planning to receive or has received a drug treatment or organ transplantation. The method includes determining an expression level of granulysin in a test sample from the subject. The subject is determined to have a good prognosis if the expression level is lower than a predetermined value, and a bad prognosis if the expression level is higher than the predetermined value. Based on the result, a physician can determine whether to proceed with the treatment or transplantation. The method can further comprise, prior to or after obtaining the sample from the subject, administering to the subject a therapeutic agent (e.g., a drug) or a transplant (e.g., a cell, a tissue) so as to determine if the subject is prone to develop ADR to the agent. For the same purpose, the method can comprise contacting the sample or other samples (e.g., e.g., samples contains T cells) with a therapeutic agent or a transplant, prior to or after determining the expression level. The predetermined value can be obtained from a normal subject or a subject having one or more of the above-described disorders (e.g., such SJS/TEN) in the manner described in the examples below. A transplant refers to an organ, a tissue, or a cell (e.g., a stem cell) taken from the body for grafting into another area of the same body or into another individual.

In another aspect, the invention features a method of treating one or more of the above-mentioned disorders. The method includes administering to a subject in need thereof an effective amount of a granulysin inhibitor. The inhibitor can be an antibody that specifically binds to granulysin, or an RNA molecule.

In yet another aspect, the invention features a method of identifying a test compound for treating one or more of the above-mentioned disorders. The method includes contacting a test compound with a cell expressing granulysin and determining an expression level of granulysin in the presence or absence of the test compound. The expression level of granulysin in the presence of the test compound, if lower than that in the absence of the test compound, indicates that the test compound can be used to treat the disorders. One can also identify a test compound for treating the disorders using a method including: providing a polypeptide having a sequence of granulysin; contacting a test compound molecule with the polypeptide; and detecting a binding between the polypeptide and the test compound. The test compound is determined to be a candidate for treating the disorders if the test compound binds to the polypeptide.

Various granulysin and its isoforms can be used in this invention. Examples of granulysin and its isoforms have been described in Krensky et al. Am. J. Transplant. 2005 August; 5(8):1789-92; Anderson et al. J Mol Biol. 2003 Jan. 10; 325(2):355-65; Gamen et al. J. Immunol. 1998 Aug. 15; 161 (4):1758-64; Pardo et al. J. Immunol. 2001 Aug. 1; 167(3): 1222-9; and Deng et al. J. Immunol. 2005 May 1; 174(9): 5243-8.

The details of one or more embodiments of the invention are set fourth in the description below. Other features, objects, and advantages of the invention will be apparent from the description and from the claims.

DETAILED DESCRIPTION

The present invention is based on an unexpected discovery that granulysin is involved in pathology of diseases associated with unwanted immunological responses or cytotoxic T cell mediated-disorders, e.g., SJS, TEN, and GVHD.

The pathogenesis of SJS/TEN is not fully understood. The manifestations of these serious life-threatening ADRs are believed to be immune-mediated since rechallenging with the same drug typically shortens the incubation period and results in more severe manifestations (Roujeau et al., Toxicology. 2005 Apr. 15; 209(2):123-9). The clinical, histopathological, immunocytological, and functional findings in SJS/TEN support the concept that SJS/TEN is a specific drug sensitivity reaction initiated by cytotoxic lymphocytes. Prior in vitro studies suggest that the drug presentation is MHC class I restricted, there is a clonal expansion of CD8+ CTLs, and these cells induce effector cytotoxic responses. The MHC-restricted presentation of a drug or its metabolites for T-cell activation is now supported by the recent findings of strong genetic association between HLA-B alleles and reaction to specific drugs. (Chung et al. Nature. 2004 Apr. 1; 428(6982): 486.). Cytotoxic T-cells are observed to infiltrate the skin lesions of SJS/TEN patients (Nassif et al., J. Allergy Clin. Immunol. 2004 November; 114(5):1209-15.) The T lymphocytes in the blister fluid and epidermis show a predominance of CD8+ phenotype (Nassif et al., J. Invest. Dermatol. 2002 April; 118(4):728-33). These observations point to a cutaneous recruitment of antigen-primed and cytotoxic T cells in the pathogenesis of SJS/TEN. Although pathogenesis of SJS/TEN is believed to be immune-mediated, the specific danger signals that lead to the massive skin cell death remains unclear.

As described herein, granulysin was found to be the key molecule responsible for the unique clinical manifestation of SJS/TEN. For example, blister fluids from skin lesions of SJS/TEN patients exhibited cytolytic activity against B-cells and keratinocytes. Global gene expression profiling of the blister cells revealed that granulysin was the most predominant cytotoxic protein. The results were verified by real-time qPCR and by immunohistochemistry. In vivo injection of granulysin into epidermis of mice induced massive skin cell death, mimicking the human pathology of SJS/TEN. Thus, granulysin, not granzyme/perforin or soluble Fas ligand (sFasL), is the key molecule responsible for the disseminated keratinocyte apoptosis and underlies the missing link of the pathogenic mechanism of SJS/TEN. The specific association of granulysin in the blister fluids of SJS/TEN also suggests that granulysin can be used for differential diagnosis of other bullous skin diseases thus avoiding skin biopsy. In addition, granulysin can be used as a target to develop novel therapeutics for these life-threatening conditions.

Diagnostic or Prognostic Methods

Within the scope of this invention is a diagnostic or prognostic method using a granulysin polypeptide or mRNA. Diagnostic and prognostic assays of the invention include method for assessing the expression level of the granulysin gene. The methods can be used to make diagnosis or prognosis with regard to autoimmune disorders, including granulysin-mediated autoimmune disorders. Autoimmune disorders are conditions caused by an immune response against the body's own tissues. A granulysin-mediated autoimmune disorder refers to autoimmune disorders associated with abnormally high level of granulysin gene expression or activity. Examples of this disorder include Stevens-Johnson syndrome, toxic epidermal necrolysis, graft-versus-host disease, Behcet disease, ankylosing spondylitis, systemic lupus erythematosus, dermatomyositis, polymyositis, and rejection disorder of organ transplantation.

The presence, level, or absence of granulysin protein or nucleic acid in a biological sample can be evaluated by obtaining a biological sample from a test subject and contacting the biological sample with a compound or an agent capable of detecting the protein or nucleic acid (e.g., mRNA and genomic DNA) that encodes granulysin such that the presence of granulysin protein or nucleic acid is detected in the biological sample. The term "biological sample" includes tissues, cells and biological fluids isolated from a subject, as well as tissues, cells and fluids present within a subject. A preferred biological sample is serum or blister fluid. The level of expression of the granulysin gene can be measured in a number of ways, including, but not limited to: measuring the mRNA encoded by the granulysin gene; measuring the amount of protein encoded by the gene; or measuring the activity of the protein encoded by the gene.

The level of mRNA corresponding to the granulysin gene in a cell can be determined both by in situ and by in vitro formats. For example, mRNA isolated from a cell can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length granulysin nucleic acid or a portion thereof, such as an oligonucleotide of at least 7, 15, 30, 50, 100, 250 or 500 nucleotides in length and sufficient to specifically hybridize under stringent conditions to granulysin mRNA or genomic DNA. The probe can be disposed on an address of an array. Other suitable probes for use in the diagnostic assays are described herein.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array described below. A skilled artisan can adapt known mRNA detection methods for use in detecting the level of mRNA encoded by the granulysin gene.

The level of mRNA in a sample that is encoded by the granulysin gene can be evaluated with nucleic acid amplification, e.g., by RT-PCR (Mullis (1987) U.S. Pat. No. 4,683,202), ligase chain reaction (Barany (1991) *Proc. Natl. Acad. Sci. USA* 88:189-193), self sustained sequence replication (Guatelli et al., (1990) *Proc. Natl. Acad. Sci. USA* 87:1874-1878), transcriptional amplification system (Kwoh et al., (1989), *Proc. Natl. Acad. Sci. USA* 86:1173-1177), Q-Beta Replicase (Lizardi et al., (1988) *Bio/Technology* 6:1197), rolling circle replication (Lizardi et al., U.S. Pat. No. 5,854,033), or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes the granulysin gene being analyzed.

In another embodiment, the methods further include contacting a control sample with a compound or agent capable of detecting granulysin mRNA, or genomic DNA, and comparing the presence of granulysin mRNA or genomic DNA in the control sample with the presence of granulysin mRNA or genomic DNA in the test sample. In still another embodiment, serial analysis of gene expression, as described in U.S. Pat. No. 5,695,937, is used to detect granulysin transcript levels.

A variety of methods can be used to determine the level of granulysin protein. In general, these methods include contacting an agent that selectively binds to the protein or its antigenic or immunogenic fragment, such as an antibody with a sample, to evaluate the level of protein in the sample. In a preferred embodiment, the antibody bears a detectable label. Antibodies can be polyclonal, or more preferably, monoclonal. An intact antibody, or a fragment thereof (e.g., Fab or $F(ab')_2$) can be used. The term "labeled," with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of detectable substances are provided herein.

The detection methods can be used to detect granulysin protein in a biological sample in vitro as well as in vivo. In vitro techniques for detection of granulysin protein include enzyme linked immunosorbent assays (ELISAs), immunoprecipitations, immunofluorescence, enzyme immunoassay (EIA), radioimmunoassay (RIA), and Western blot analysis. In vivo techniques for detection of granulysin protein include introducing into a subject a labeled anti-granulysin antibody. For example, the antibody can be labeled with a radioactive marker whose presence and location in a subject can be detected by standard imaging techniques. In another embodiment, the sample is labeled, e.g., biotinylated and then contacted to the antibody, e.g., an anti-granulysin antibody positioned on an antibody array. The sample can be detected, e.g., with avidin coupled to a fluorescent label.

In another embodiment, the methods further include contacting the control sample with a compound or agent capable of detecting granulysin protein, and comparing the presence of granulysin protein in the control sample with the presence of granulysin protein in the test sample.

The invention also includes kits for detecting the presence of granulysin in a biological sample. For example, the kit can include a compound or agent capable of detecting granulysin protein or mRNA in a biological sample; and a standard. The compound or agent can be packaged in a suitable container. The kit can further comprise instructions for using the kit to detect granulysin protein or nucleic acid.

For antibody-based kits, the kit can include: (1) a first antibody (e.g., attached to a solid support) which binds to a polypeptide corresponding to a marker of the invention; and, optionally, (2) a second, different antibody which binds to either the polypeptide or the first antibody and is conjugated to a detectable agent.

For oligonucleotide-based kits, the kit can include: (1) an oligonucleotide, e.g., a detectably labeled oligonucleotide, which hybridizes to a nucleic acid sequence encoding a polypeptide corresponding to a marker of the invention or (2) a pair of primers useful for amplifying a nucleic acid molecule corresponding to a marker of the invention. The kit can also include a buffering agent, a preservative, or a protein stabilizing agent. The kit can also include components necessary for detecting the detectable agent (e.g., an enzyme or a substrate). The kit can also contain a control sample or a series of control samples which can be assayed and compared to the test sample contained. Each component of the kit can be enclosed within an individual container and all of the various containers can be within a single package, along with instructions for interpreting the results of the assays performed using the kit.

The diagnostic methods described herein can identify subjects having, or at risk of developing, a disease or disorder associated with misexpressed or aberrant or unwanted granulysin expression or activity. As used herein, the term "unwanted" includes an unwanted phenomenon involved in a biological response such as cytotoxic T cell mediated-disorder (e.g., Stevens-Johnson syndrome, toxic epidermal necrolysis, or graft-versus-host disease).

In one embodiment, a disease or disorder associated with aberrant or unwanted granulysin expression or activity is identified. A test sample is obtained from a subject and granulysin protein or nucleic acid (e.g., mRNA or genomic DNA) is evaluated, wherein the level, e.g., the presence of granulysin protein or nucleic acid is diagnostic for a subject having or at risk of developing a disease or disorder associated with aberrant or unwanted granulysin expression or activity. As used herein, a "test sample" refers to a biological sample obtained from a subject of interest, including a biological fluid (e.g., blister fluid or serum), cell sample, or tissue.

The prognostic assays described herein can be used to determine whether a subject, once administered an agent (e.g., an agonist, antagonist, peptidomimetic, protein, peptide, nucleic acid, small molecule, or other drug candidate) or transplanted with a cell, a tissue, or an organ to treat a disease, will develop ADRs or other disorders, e.g., a graft-versus-host disease.

Also featured is a method of evaluating a sample from a subject. The method includes providing a sample and determining a gene expression profile of the sample, wherein the profile includes a value representing the level of granulysin expression. The method can further include comparing the value or the profile (i.e., multiple values) to a reference value or reference profile. The gene expression profile of the sample can be obtained by any of the methods described herein (e.g., by providing a nucleic acid from the sample and contacting the nucleic acid to an array). The method can be used to diagnose a cytotoxic T cell mediated disorder in a subject wherein an increase in granulysin expression is an indication that the subject has or is disposed to having the disorder. The method can be used to monitor a treatment for the disorder in a subject. For example, the gene expression profile can be determined for a sample from a subject undergoing treatment. The profile can be compared to a reference profile or to a profile obtained from the subject prior to treatment or prior to onset of the disorder (see, e.g., Golub et al. (1999) Science 286:531).

Drug Screening

As discussed therein, granulysin is involved in a cytotoxic T cell-mediated disorder. Accordingly, a granulysin inhibitor can be used in treating the disorder. The invention features a method for identifying a granulysin inhibitor for treating a cytotoxic T cell-mediated disorder. A granulysin inhibitor can be obtained from commercial suppliers or identified according to the methods described below or any other methods well known in the art.

Candidate compounds (e.g., proteins, peptides, peptidomimetics, peptoids, antibodies, small molecules, or other drugs) can be obtained using any of the numerous approaches in combinatorial library methods known in the art. Such libraries include: peptide libraries, peptoid libraries (libraries of molecules having the functionalities of peptides, but with a novel, non-peptide backbone that is resistant to enzymatic degradation); spatially addressable parallel solid phase or solution phase libraries; synthetic libraries obtained by deconvolution or affinity chromatography selection; and the "one-bead one-compound" libraries. See, e.g., Zuckermann et al. 1994, J. Med. Chem. 37:2678-2685; and Lam, 1997, Anticancer Drug Des. 12:145. Examples of methods for the synthesis of molecular libraries can be found in, e.g., DeWitt et al., 1993, PNAS USA 90:6909; Erb et al., 1994, PNAS USA 91:11422; Zuckermann et al., 1994, J. Med. Chem. 37:2678; Cho et al., 1993, Science 261:1303; Carrell et al., 1994, Angew. Chem. Int. Ed. Engl. 33:2059; Carell et al., 1994, Angew. Chem. Int. Ed. Engl. 33:2061; and Gallop et al., 1994 J. Med. Chem. 37:1233. Libraries of compounds may be presented in solution (e.g., Houghten, 1992, Biotechniques 13:412-421), or on beads (Lam, 1991, Nature 354:82-84), chips (Fodor, 1993, Nature 364:555-556), bacteria (U.S. Pat. No. 5,223,409), spores (U.S. Pat. No. 5,223,409), plasmids (Cull et al., 1992, PNAS USA 89:1865-1869), or phages (Scott and Smith 1990, Science 249:386-390; Devlin, 1990, Science 249:404-406; Cwirla et al., 1990, PNAS USA 87:6378-6382; Felici 1991, J. Mol. Biol. 222:301-310; and U.S. Pat. No. 5,223,409).

To identify a granulysin inhibitor, one can contact a candidate compound with a system containing granulysin. The system can be a cell-free system or a cell-containing system, e.g., an in vitro cell line model or an in vivo animal model. In a cell-containing system, cells can naturally express the granulysin gene, or can be modified to express a recombinant nucleic acid. The recombinant nucleic acid can contain the granulysin gene coding region fused to a heterologous promoter or a granulysin gene promoter sequence fused to a reporter gene. One then measures the expression level of the granulysin gene.

The expression level can be determined at either the mRNA level or at the protein level. Methods of measuring mRNA levels in a tissue sample or a body fluid are well known in the art. To measure mRNA levels, cells can be lysed and the levels of mRNA in the lysates or in RNA purified or semi-purified from the lysates can be determined by, e.g., hybridization assays (using detectably labeled gene-specific DNA or RNA probes) and quantitative or semi-quantitative RT-PCR (using appropriate gene-specific primers). Alternatively, quantitative or semi-quantitative in situ hybridization assays can be carried out using tissue sections or unlysed cell suspensions, and detectably (e.g., fluorescent or enzyme) labeled DNA or RNA probes. Additional mRNA-quantifying methods include RNA protection assay (RPA) and SAGE.

Methods of measuring protein levels in a tissue sample or a body fluid are also known in the art. Many such methods employ antibodies (e.g., monoclonal or polyclonal antibodies) that bind specifically to a target protein. In such assays, the antibody itself or a secondary antibody that binds to it can be detectably labeled. Alternatively, the antibody can be conjugated with biotin, and detectably labeled avidin (a polypeptide that binds to biotin) can be used to detect the presence of the biotinylated antibody. Combinations of these approaches (including "multi-layer sandwich" assays) can be used to enhance the sensitivity of the methodologies. Some of these protein-measuring assays (e.g., ELISA or Western blot) can be applied to body fluids or to lysates of cells, and others (e.g., immunohistological methods or fluorescence flow cytometry) applied to histological sections or unlysed cell suspensions. Methods of measuring the amount of label depend on the nature of the label and are well known in the art. Appropriate labels include radionuclides (e.g., $^{125}$I, $^{131}$I, $^{35}$S, $^{3}$H, or $^{32}$P), enzymes (e.g., alkaline phosphatase, horseradish peroxidase, luciferase, or β-glactosidase), fluorescent moieties or proteins (e.g., fluorescein, rhodamine, phycoerythrin, GFP, or BFP), or luminescent moieties (e.g., Qdot™ nanoparticles supplied by the Quantum Dot Corporation, Palo Alto, Calif.). Other applicable assays include quantitative immunoprecipitation or complement fixation assays.

To determine the ability of a candidate compound to inhibit granulysin, one compares the level obtained in the manner described above with a control level obtained in the absence of the candidate compound. If the level or activity is lower than the control, the compound is identified as being effective for treating a cytotoxic T cell-mediated disorder.

One can further verify the efficacy of a compound thus-identified using an animal model. For example, to verify a compound for treating a cytotoxic T cell-mediated disorder, one can administer the compound to nude mice that have received granulysin and exam them according to the method describe below in the Example section or other standard techniques. Any statistically significant improvement of the skin conditions of the nude mice indicates the compound is a candidate for treating the cytotoxic T cell-mediated disorder.

The present invention provides antibody binding to granulysin. There is no particular restriction as to the form of the antibody and the present invention includes polyclonal antibodies, as well as monoclonal antibodies. The antiserum obtained by immunizing animals such as rabbits with a protein of the present invention, as well polyclonal and monoclonal antibodies of all classes, human antibodies, and humanized antibodies made by genetic engineering, is also included.

The term "antibody" refers to an immunoglobulin molecule or immunologically active portion thereof, i.e., an antigen-binding portion. It refers to a protein comprising at least one, and preferably two, heavy (H) chain variable regions ($V_H$), and at least one and preferably two light (L) chain variable regions ($V_L$). The $V_H$ and $V_L$ regions can be further subdivided into regions of hypervariability, termed "complementarity determining regions" ("CDR"), interspersed with regions that are more conserved, termed "framework regions" (FR). The extent of the framework region and CDR's has been precisely defined (see, Kabat et al. (1991) *Sequences of Proteins of Immunological Interest, Fifth Edition,* U.S. Department of Health and Human Services, NIH Publication No. 91-3242, and Chothia et al. (1987) J. Mol. Biol. 196:901-917, which are incorporated herein by reference). Each $V_H$ and $V_L$ is composed of three CDR's and four FRs, arranged from amino-terminus to carboxy-terminus in the following order: FR1, CDR1, FR2, CDR2, FR3, CDR3, FR4.

The antibody can further include a heavy and light chain constant region, to thereby form a heavy and light immunoglobulin chain, respectively. The heavy chain constant region is comprised of three domains, CH1, CH2 and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system.

As used herein, the term "immunoglobulin" refers to a protein consisting of one or more polypeptides substantially encoded by immunoglobulin genes. The recognized human immunoglobulin genes include the kappa, lambda, alpha (IgA1 and IgA2), gamma (IgG1, IgG2, IgG3, IgG4), delta, epsilon and mu constant region genes, as well as the myriad immunoglobulin variable region genes. Full-length immunoglobulin "light chains" (about 25 KDa or 214 amino acids) are encoded by a variable region gene at the NH2-terminus (about 110 amino acids) and a kappa or lambda constant region gene at the COOH-terminus. Full-length immunoglobulin "heavy chains" (about 50 KDa or 446 amino acids), are similarly encoded by a variable region gene (about 116 amino acids) and one of the other aforementioned constant region genes, e.g., gamma (encoding about 330 amino acids).

The term "antigen-binding fragment" of an antibody (or "antibody portion," or "fragment") refers to one or more fragments of a full-length antibody that retain the ability to specifically bind to the antigen, e.g., EGFR or CD3 polypeptide or fragment thereof. Examples of antigen-binding fragments of the antibody include, but are not limited to: (i) a Fab fragment, a monovalent fragment consisting of the $V_L$, $V_H$, $C_L$ and $C_{H1}$ domains; (ii) a $F(ab')_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) *Nature* 341:544-546), which consists of a $V_H$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *Proc. Nati. Acad. Sci. USA* 85:5879-5883). Such single chain antibodies are also encompassed within the term "antigen-binding fragment" of an antibody. These antibody fragments can be obtained using conventional techniques known to those with skill in the art, and the fragments are screened for utility in the same manner as are intact antibodies.

Suitable antibody can be a monoclonal antibody. In other embodiments, the antibody can be recombinantly produced, e.g., produced by phage display or by combinatorial methods. Phage display and combinatorial methods for generating antibodies are known in the art (see e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370-1372; Hay et al. (1992) *Hum Antibod Hybridomas* 3:81-85; Huse et al. (1989) *Science* 246:1275-1281; Griffths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; and Barbas et al. (1991) *PNAS* 88:7978-7982, the contents of all of which are incorporated by reference herein).

In one embodiment, the antibody is a fully human antibody (e.g., an antibody made in a mouse which has been genetically engineered to produce an antibody from a human immunoglobulin sequence), or a non-human antibody, e.g., a rodent (mouse or rat), goat, primate (e.g., monkey), camel antibody. Preferably, the non-human antibody is a rodent (mouse or rat antibody). Methods of producing rodent antibodies are known in the art.

Human monoclonal antibodies can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 *Nature* 368:856-859; Green, L. L. et al. 1994 *Nature Genet.* 7:13-21; Morrison et al. 1994 *Proc. Natl. Acad. Sci. USA* 81:6851-6855; Bruggeman et al. 1993 *Year Immunol* 7:33-40; Tuaillon et al. 1993 *PNAS* 90:3720-3724; Bruggeman et al. 1991 *Eur J Immunol* 21:1323-1326).

An antibody can be one in which the variable region, or a portion thereof, e.g., the CDR's, are generated in a non-human organism, e.g., a rat or mouse. Chimeric, CDR-grafted, and humanized antibodies can be used. Antibodies generated in a non-human organism, e.g., a rat or mouse, and then modified, e.g., in the variable framework or constant region, to decrease antigenicity in a human are within the invention.

Chimeric antibodies can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125,023; Better et al. (1988 *Science* 240:1041-1043); Liu et al. (1987) *PNAS* 84:3439-3443; Liu et al., 1987, *J. Immunol.* 139:3521-3526; Sun et al. (1987) *PNAS* 84:214-218; Nishimura et al., 1987, *Canc. Res.* 47:999-1005; Wood et al. et al (1985) *Nature* 314:446-449; and Shaw et al., 1988, *J. Natl Cancer Inst.* 80:1553-1559).

A humanized or CDR-grafted antibody will have at least one or two but generally all three recipient CDR's (of heavy and or light immuoglobulin chains) replaced with a donor CDR. The antibody may be replaced with at least a portion of a non-human CDR or only some of the CDR's may be replaced with non-human CDR's. It is only necessary to replace the number of CDR's required for binding of the humanized antibody or a fragment thereof. Preferably, the donor will be a rodent antibody, e.g., a rat or mouse antibody, and the recipient will be a human framework or a human consensus framework. Typically, the immunoglobulin providing the CDR's is called the "donor" and the immunoglobulin providing the framework is called the "acceptor." In one embodiment, the donor immunoglobulin is a non-human (e.g., rodent). The acceptor framework is a naturally-occurring (e.g., a human) framework or a consensus framework, or a sequence about 85% or higher, preferably 90%, 95%, 99% or higher identical thereto. As used herein, the term "consensus sequence" refers to the sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

An antibody can be humanized by methods known in the art. Humanized antibodies can be generated by replacing sequences of the Fv variable region which are not directly involved in antigen binding with equivalent sequences from human Fv variable regions. General methods for generating humanized antibodies are provided by Morrison, S. L., 1985, *Science* 229:1202-1207, by Oi et al., 1986, *BioTechniques* 4:214, and by Queen et al. U.S. Pat. Nos. 5,585,089, 5,693,761 and 5,693,762, the contents of all of which are hereby incorporated by reference. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from a hybridoma producing an antibody against a polypeptide of interest or fragment thereof.

The recombinant DNA encoding the humanized antibody, or fragment thereof, can then be cloned into an appropriate expression vector.

Also can be fused to the scaffold are humanized antibodies in which specific amino acids have been substituted, deleted or added. Preferred humanized antibodies have amino acid substitutions in the framework region, such as to improve binding to an antigen. For example, a humanized antibody will have framework residues identical to the donor framework residue or to another amino acid other than the recipient framework residue. To generate such antibodies, a selected, small number of acceptor framework residues of the humanized immunoglobulin chain can be replaced by the corresponding donor amino acids. Preferred locations of the substitutions include amino acid residues adjacent to the CDR, or which are capable of interacting with a CDR. Criteria for selecting amino acids from the donor are described in U.S. Pat. No. 5,585,089, the contents of which are hereby incorporated by reference. Other techniques for humanizing antibodies are described in Padlan et al. EP 519596 A1.

Treatment Methods

The invention also features a method for treating one or more of the above described disorders. A subject to be treated can be identified by standard diagnosing techniques for such a disorder. Optionally, the subject can then be examined for the gene expression or activity level of the granulysin polypeptide by methods described above. If the gene expression or activity level is higher in a sample from the subject than that in a sample from a normal person, the subject is a candidate for treatment with an effective amount of a granulysin inhibitor.

"Treating" refers to administration of a compound to a subject, who has one or more of the above-described disorders, with the purpose to cure, alleviate, relieve, remedy, prevent, or ameliorate the disorder, the symptom of the disorder, the disease state secondary to the disorder, or the predisposition toward the disorder. An "effective amount" refers to an amount of the compound that is capable of producing a medically desirable result, e.g., as described above, in a treated subject. The treatment method can be performed in vivo or ex vivo, alone or in conjunction with other drugs or therapy.

In an in vivo approach, a granulysin inhibitor is administered to a subject. Generally, the compound is suspended in a pharmaceutically-acceptable carrier (e.g., physiological saline) and administered orally or by intravenous infusion, or injected or implanted subcutaneously, intramuscularly, intrathecally, intraperitoneally, intrarectally, intravaginally, intranasally, intragastrically, intratracheally, or intrapulmonarily. For treatment of a skin disorder, such as SJS and TEN, the compound can be delivered topically.

The dosage required depends on the choice of the route of administration; the nature of the formulation; the nature of the patient's illness; the subject's size, weight, surface area, age, and sex; other drugs being administered; and the judgment of the attending physician. Suitable dosages are in the range of 0.01-100 mg/kg. Variations in the needed dosage are to be expected in view of the variety of compounds available and the different efficiencies of various routes of administration. For example, oral administration would be expected to require higher dosages than administration by i.v. injection. Variations in these dosage levels can be adjusted using standard empirical routines for optimization as is well understood in the art. Encapsulation of the compound in a suitable delivery vehicle (e.g., polymeric microparticles or implantable devices) may increase the efficiency of delivery, particularly for oral delivery.

Alternatively, a polynucleotide containing a nucleic acid sequence encoding an inhibitor of a granulysin can be delivered to a subject. The nucleic acid sequence can encode an anti-granulysin antibody, an anti-sense RNA, or a small interference RNA (e.g., an RNAi agent) that targets granulysin and inhibits its expression or activity.

The term "RNAi" or "RNA interference" refers to a sequence-specific or selective process by which a target molecule (e.g., a target gene, protein or RNA) is down-regulated. Within the scope of this invention is utilization of RNAi featuring degradation of RNA molecules (e.g., within a cell). Degradation is catalyzed by an enzymatic, RNA-induced silencing complex (RISC). RNAi occurs in cells naturally to remove foreign RNAs (e.g., viral RNAs). Natural RNAi proceeds via fragments cleaved from free double-stranded RNA, which directs the degradative mechanism. Alternatively, RNAi can be initiated by the hand of man, for example, to silence the expression of target genes.

The term "RNAi agent" refers to an RNA (or analog thereof), having sufficient sequence complementarity to a target RNA (i.e., the RNA being degraded) to direct RNAi. A RNA agent having a "sequence sufficiently complementary to a target RNA sequence to direct RNAi" means that the RNA agent has a sequence sufficient to trigger the destruction of the target RNA by the RNAi machinery (e.g., the RISC complex) or process. A RNA agent having a "sequence sufficiently complementary to a target RNA sequence to direct RNAi" also means that the RNA agent has a sequence sufficient to trigger the translational inhibition of the target RNA by the RNAi machinery or process. A RNA agent can also have a sequence sufficiently complementary to a target RNA encoded by the target DNA sequence such that the target DNA sequence is chromatically silenced. In other words, the RNA agent has a sequence sufficient to induce transcriptional gene silencing, e.g., to down-modulate gene expression at or near the target DNA sequence, e.g., by inducing chromatin structural changes at or near the target DNA sequence. The term "RNA" or "RNA molecule" or "ribonucleic acid molecule" refers to a polymer of ribonucleotides. The term "DNA" or "DNA molecule" or deoxyribonucleic acid molecule" refers to a polymer of deoxyribonucleotides. DNA and RNA can be synthesized naturally (e.g., by DNA replication or transcription of DNA, respectively). RNA can be post-transcriptionally modified. DNA and RNA can also be chemically synthesized. DNA and RNA can be single-stranded (i.e., ssRNA and ssDNA, respectively) or multi-stranded (e.g., double-stranded, i.e., dsRNA and dsDNA, respectively).

The polynucleotide can be delivered by the use of polymeric, biodegradable microparticle or microcapsule delivery devices known in the art. Another way to achieve uptake of the nucleic acid is using liposomes, prepared by standard methods. The polynucleotide can be incorporated alone into these delivery vehicles or co-incorporated with tissue-specific antibodies. Alternatively, one can prepare a molecular conjugate composed of a plasmid or other vector attached to poly-L-lysine by electrostatic or covalent forces. Poly-L-lysine binds to a ligand that can bind to a receptor on target cells (Cristiano, et al., 1995, J. Mol. Med. 73:479). Alternatively, tissue specific targeting can be achieved by the use of tissue-specific transcriptional regulatory elements that are known in the art. Delivery of "naked DNA" (i.e., without a delivery vehicle) to an intramuscular, intradermal, or subcutaneous site is another means to achieve in vivo expression.

In the above-mentioned polynucleotides, e.g., expression vectors, the nucleic acid sequence encoding an inhibitor of granulysin is operatively linked to a promoter or enhancer-promoter combination. Suitable expression vectors include plasmids and viral vectors such as herpes viruses, retroviruses, vaccinia viruses, attenuated vaccinia viruses, canary pox viruses, adenoviruses and adeno-associated viruses.

As is well known in the art, the dosage for a patient depends upon various factors as described above. Dosages will vary, but a preferred dosage for administration of polynucleotide is about $10^6$ to $10^{12}$ copies of the polynucleotide molecule. This dose can be repeatedly administered as needed. Routes of administration can be any of those listed above.

In an ex vivo strategy, treating a subject with a cytotoxic T cell-mediated disorder involves transfecting or transducing cells obtained from the subject with a polynucleotide encoding a granulysin inhibitor. Cells can be transfected in vitro with a vector designed to insert, by homologous recombination, a new, active promoter upstream of the transcription start site of a naturally occurring endogenous granulysin inhibitor gene in the cells' genome. After selection and expansion of cell that express the granulysin inhibitor at a desired level, the transfected or transduced cells are then returned to the subject. Examples of the cells include neural cells, hemopoietic cells (e.g., bone marrow cells, macrophages, monocytes, dendritic cells, T cells, or B cells), fibroblasts, epithelial cells, endothelial cells, keratinocytes, or muscle cells. Such cells act as a source of the granulysin inhibitor for as long as they survive in the subject.

The just-described ex vivo method includes the steps of harvesting cells from a subject, culturing the cells, transducing them with an expression vector, and maintaining the cells under conditions suitable for expression of a granulysin inhibitor. The transduction step is accomplished by any standard means used for ex vivo gene therapy, including calcium phosphate, lipofection, electroporation, viral infection, and biolistic gene transfer. Alternatively, liposomes or polymeric microparticles can be used. Cells that have been successfully transduced can then be selected, for example, for expression of the granulysin inhibitor. The cells may then be injected or implanted into the subject.

Also within the scope of the invention is a packaged product including a container, an effective amount of a granulysin inhibitor and a legend associated with the container and indicating administration of the inhibitor for treating a subject suffering from or being at risk for developing a cytotoxic T cell-mediated disorder. The inhibitor can be admixed with a pharmaceutically acceptable carrier, including a solvent, a dispersion medium, a coating, an antibacterial and antifungal agent, and an isotonic and absorption-delaying agent.

The inhibitor can be formulated into dosage forms for different administration routes utilizing conventional methods. For example, it can be formulated in a capsule, a gel seal, or a tablet for oral administration. Capsules can contain any standard pharmaceutically acceptable materials such as gelatin or cellulose. Tablets can be formulated in accordance with conventional procedures by compressing mixtures of the inhibitor with a solid carrier and a lubricant. Examples of solid carriers include starch and sugar bentonite. The inhibitor can also be administered in a form of a hard shell tablet or a capsule containing a binder, e.g., lactose or mannitol, a conventional filler, and a tableting agent. The inhibitor can be administered via the parenteral route. Examples of parenteral dosage forms include aqueous solutions, isotonic saline or 5% glucose of the active agent, or other well-known pharmaceutically acceptable excipient. Cyclodextrins, or other solubilizing agents well known to those familiar with the art, can be utilized as pharmaceutical excipients for delivery of the therapeutic agent.

Compositions

Within the scope of this invention is a pharmaceutical composition that contains a pharmaceutically acceptable carrier and an effective amount of a granulysin inhibitor described herein. The pharmaceutical composition can be used to treat a cytotoxic T cell-mediated disorder. The pharmaceutically acceptable carrier includes a solvent, a dispersion medium, a coating, an antibacterial and antifungal agent, and an isotonic and absorption delaying agent.

A pharmaceutical composition of the invention can be formulated into dosage forms for different administration routes utilizing conventional methods. For example, it can be formulated in a capsule, a gel seal, or a tablet for oral administration. Capsules can contain any standard pharmaceutically acceptable materials such as gelatin or cellulose. Tablets can be formulated in accordance with conventional procedures by compressing mixtures of the composition with a solid carrier and a lubricant. Examples of solid carriers include starch and sugar bentonite. The composition can also be administered in a form of a hard shell tablet or a capsule containing a binder, e.g., lactose or mannitol, a conventional filler, and a tableting agent. The pharmaceutical composition can be administered via the parenteral route. Examples of parenteral dosage forms include aqueous solutions, isotonic saline or 5% glucose of the active agent, or other well-known pharmaceutically acceptable excipient. Cyclodextrins, or other solubilizing agents well known to those familiar with the art, can be utilized as pharmaceutical excipients for delivery of the therapeutic agent.

A composition described herein can also contain a safe and effective amount of a dermatologically acceptable carrier that is suitable for topical application to the skin. It enables the essential materials and optional components in it to be delivered to the skin at an appropriate concentration. The carrier can thus act as a diluent, dispersant, solvent, or the like to ensure that the active materials are applied to and distributed evenly over the selected target at an appropriate concentration. The carrier can be solid, semi-solid, or liquid. Preferably, the carrier is in the form of a lotion, a cream, or a gel, more preferably one that has a sufficient thickness or yield point to prevent the active materials from sedimenting. The carrier can itself be inert or it can possess dermatological benefits of its own. The carrier should also be physically and, chemically compatible with the essential components described herein, and should not unduly impair stability, efficacy, or other use benefits associated with the compositions described herein.

The type of carrier utilized in the present invention depends on the type of product form desired for the composition. The topical compositions useful in the subject invention may be made into a wide variety of product forms such as are known in the art. These include, but are not limited to, lotions, creams, gels, sticks, sprays, ointments, pastes, and mousses. These product forms may comprise several types of carriers including, but not limited to, solutions, aerosols, emulsions, gels, solids, and liposomes.

Preferred carriers can contain a dermatologically acceptable, hydrophilic diluent. Suitable hydrophilic diluents include water, organic hydrophilic diluents, such as $C_1$-$C_4$ monohydric alcohols and low molecular weight glycols and polyols (including propylene glycol, polyethylene glycol of, e.g., MW 200-600), polypropylene glycol of, e.g. MW 425-2025, glycerol, butylene glycol, 1,2,4-butanetriol, sorbitol esters, 1,2,6-hexanetriol, ethanol, iso-propanol, sorbitol esters, ethoxylated ethers, propoxylated ethers, and combinations thereof. The composition preferably comprises at least about 60% of the hydrophilic diluent.

Preferred carriers also contain an emulsion having a hydrophilic phase, especially an aqueous phase, and a hydrophobic phase e.g., a lipid, oil, or oily material. As well known to one skilled in the art, the hydrophilic phase will be dispersed in the hydrophobic phase, or vice versa, to form respectively hydrophilic or hydrophobic dispersed and continuous phases, depending on the composition ingredients. The term “dispersed phase,” a term well-known to one skilled in the art, refers to a phase that exists as small particles or droplets suspended in and surrounded by a continuous phase. The dispersed phase is also known as the internal or discontinuous phase. The emulsion may be or contain (e.g., in a triple or other multi-phase emulsion) an oil-in-water emulsion or a water-in-oil emulsion such as a water-in-silicone emulsion. Oil-in-water emulsions typically comprise from about 1% to about 50% (preferably about 1% to about 30%) of the dispersed hydrophobic phase and from about 1% to about 99% (preferably from about 40% to about 90%) of the continuous hydrophilic phase; water-in-oil emulsions typically comprise from about 1% to about 98% (preferably from about 40% to about 90%) of the dispersed hydrophilic phase and from about 1% to about 50% (preferably about 1% to about 30%) of the continuous hydrophobic phase. The emulsion may also comprise a gel network, such as described in G. M. Eccleston, Application of Emulsion Stability Theories to Mobile and Semisolid O/W Emulsions, Cosmetics & Toiletries, Vol. 101, November 1996, pp. 73-92, incorporated herein by reference. Preferred compositions herein are oil-in-water emulsions.

Preferred examples of the topical composition of this invention have an apparent viscosity of from about 5,000 to about 200,000 mPa·s (centipoise). For example, preferred lotions have an apparent viscosity of from about 10,000 to about 40,000 mPa·s; preferred creams have an apparent viscosity of from about 30,000 to about 160,000 mPa·s. Apparent viscosity can be determined using a Brookfield DVII RV viscometer, spindle TD, at 5 rpm, or the equivalent thereof. The viscosity is determined on a composition after the composition has been allowed to stabilize following its preparation, generally at least 24 hours under conditions of 25° C.±1° C. and ambient pressure after preparation of the composition. Apparent viscosity is measured with the composition at a temperature of 25° C.±1° C., after 30 seconds spindle rotation.

The topical composition of the present invention is usually formulated to have a pH of 9.5 or below and in general have a pH in the range from about 4.5 to about 9, more preferably from about 5 to about 8.5. Some examples, particularly those containing an additional active agent such as salicylic acid, require a lower pH in order for the additional active to be fully efficacious. These compositions are usually formulated to have a pH of from about 2.5 to about 5, more preferably from about 2.7 to about 4.

The topical compositions may contain a wide variety of optional components, provided that such optional components are physically and chemically compatible with the essential components described herein, and do not unduly impair stability, efficacy, or other use benefits associated with the compositions. Optional components may be dispersed, dissolved, or the like in the carrier of the present compositions.

Exemplary optional components include emollients, oil absorbents, antimicrobial agents, binders, buffering agents, denaturants, cosmetic astringents, external analgesics, film formers, humectants, opacifying agents, perfumes, pigments, skin soothing and healing agents, preservatives, propellants, skin penetration enhancers, solvents, suspending agents, emulsifiers, cleansing agents, thickening agents, solubilising agents, waxes, sunscreens, sunless tanning agents, antioxidants and/or radical scavengers, chelating agents, anti-acne agents, anti-inflammatory agents, desquamation agents/exfoliants, organic hydroxy acids, vitamins, and natural extracts. Examples of such materials are described in Harry's Cosmeticology, 7th Ed., Harry & Wilkinson (Hill Publishers, London 1982); in Pharmaceutical Dosage Forms—Disperse Systems; Lieberman, Rieger & Banker, Vols. 1 (1988) & 2 (1989); Marcel Decker, Inc.; in The Chemistry and Manufacture of Cosmetics, 2nd. Ed., deNavarre (Van Nostrand 1962-1965); and in The Handbook of Cosmetic Science and Technology, 1st Ed. Knowlton & Pearce (Elsevier 1993) can also be used in the present invention.

The topical composition of the present invention is generally prepared by conventional methods such as are known in the art of making topical compositions. Such methods typically involve mixing of the ingredients in one or more steps to a relatively uniform state, with or without heating, cooling, application of vacuum, and the like.

The topical composition is useful for treating or slowing down the onset of diseases that injure or affect the skin. It can also be used for regulating or improving skin condition. To use a topical composition of this invention, one can topically apply to the skin a safe and effective amount of the composition. The applied amount, the frequency of application and the period of use vary widely depending upon the active levels of a given composition and the level of regulation desired.

A wide range of quantities of the compositions of the present invention can be employed to provide a skin appearance and/or feel benefit. Quantities of the compositions typically applied per application are from about 0.1 $mg/cm^2$ to about 10 $mg/cm^2$, e.g., 2 $mg/cm^2$. Typically, a composition can be used once per day. However, application rates can vary from about once per week up to about three times per day or more.

The topical composition of this invention provides a visible improvement in skin condition essentially immediately following application of the composition to the skin. Such immediate improvement involves coverage or masking of skin imperfections such as textural discontinuities (including those associated with skin aging, e.g., enlarged pores), or providing a more even skin tone or color. The compositions of the invention also provide visible improvements in skin condition following chronic topical application. "Chronic topical application" involves continued topical application of a composition over an extended period during the subject's lifetime, preferably for a period of at least about one week, one month, three months, six months, or one year. Chronic regulation of skin condition involves improvement of skin condition following multiple topical applications.

Regulating skin conditions is preferably performed by applying a composition in the form of a skin lotion, cream, cosmetic, or the like which is intended to be left on the skin for an extended period for some aesthetic, prophylactic, therapeutic or other benefit (i.e., a "leave-on" composition). As used herein, "leave-on" compositions exclude rinse-off skin cleansing products. After applying the composition to the skin, the leave-on composition is preferably left on the skin for a period of at least about 15 minutes, 30 minutes, 1 hour, or up to about 12 hours.

The efficacy of an inhibitor or a composition described herein can be evaluated both in vitro and in vivo. For example, the inhibitor can be tested for its ability to repress gene expression or activity of granulysin in vitro. For in vivo studies, the inhibitor can be injected into an animal (e.g., an animal model) and its effects on a cytotoxic T cell-mediated disorder are then accessed. Based on the results, an appropriate dosage range and administration route can be determined.

The above-described granulysin inhibitor can also be used in treating other diseases that are associated with abnormally high level of granulysin gene expression or activity. A subject to be treated can be identified by methods known in the art or by determining the gene expression or activity level of the granulysin polypeptide in a sample prepared from a subject as described above. If the gene expression or activity level of the polypeptide is higher in the sample from the subject than that in a sample from a normal person, the subject is a candidate for treatment with an effective amount of a granulysin inhibitor.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLE

Clinical Samples

Blister cells and fluid were collected from patients with SJS/TEN, and from patients with burn injuries at Chang Gung Memorial Hospital, Taiwan. All these patients were diagnosed by clinical presentation and histopathologic findings by methods known in the art (Roujeau et al. J. Invest. Dermatol. 1994 June; 102(6):28S-30S). The fresh blister cells for expression analyses were obtained by harvesting the cells immediately from skin tissue used for histological diagnosis of SJS/TEN. Blister fluid was obtained on admission through puncture of several blisters. In addition, skin biopsies of 5 patients with drug-induced maculopapular eruption (MPE) were obtained. Blood leucocytes were obtained from 10 healthy control subjects, and from all of the patients with SJS/TEN or MPE.

Immunophenotypes of Cells Present in Blister Fluid of Skin Lesions

The cell types in the blister were examined by flowcytometry. Antibodies and reagents used for immunostaining of blister cells were described as below. Anti-CD3, -CD4, -CD8, -CD20 and -CD56 monoclonal antibodies (mAb) were purchased from BD Biosciences. Phenotypic analysis was performed on thawed blister cells. After incubation with GolgiStop (BD Biosciences), the cells were fixed with a BD Cytofix/Cytoperm solution for 20 minutes at 4° C. and incubated in PBS containing 10% human serum. Then the cells were stained with distinct fluorescent monoclonal antibody: anti-CD3, -CD4, -CD8, and -CD56 mAb for 20 minutes at 4° C. Anti-granulysin mAB (RB1; MBL) was obtained from MBL international corporation. To visualize granulysin in cells, cells were first stained with anti-granulysin mAB (RB1; MBL) for 1 hour at 4° C. and then incubated with secondary FITC- and PE-conjugated anti-mouse mAb for 1 hour at 4° C.

Determination of Cytotoxicity of Blister Cells and Fluids In Vitro

For cytotoxic assay, blister cells from SJS/TEN patients were washed and co-incubated with autologous EBV-transformed B cells for 4 hours at 37° C. The cells were then washed and stained with FITC-labeled anti-CD20 mAb and PE-conjugated Annexin-V (BD Biosciences) for 20 minutes at 4° C. To determine cytotoxic activity of blister fluids, a target keratinocyte cell line (CCD 1106 KERTr) was used. The cells were seeded in a 12-well plate, and then incubated with blister fluids at different concentrations (0%, 1%, 10%, and 50%) in 37° C. for 24 hours.

After incubation with blister fluids, target cells were stained with annexin-V for 20 minutes at 25° C. The annexin-V (+) keratinocyts was measured by flow cytometery. Cell viability was determined by a modified version of the MTT reduction method of Mosmann (Alley et al. Cancer Res. 1988 Feb. 1; 48(3):589-601). The result was expressed as a percentage of that in control cultures. Cell death was determined by the trypan blue exclusion test.

Microarray Experiments

Total RNA was isolated from blister cells or peripheral blood mononuclear cell (PBMC), and then subjected to microarray analysis using the Human Genome U133 Plus 2.0 array) according to the manufacturers' directions. The array includes over 47,000 transcripts (Affymetrix). The QA/QC of raw data was evaluated by Affymetrix Statistical MAS5. Data was analyzed using Genedata software (Genedata expressionist) with setting the median as a reference value of 10000. To evaluate genes with high expression levels, the maximum P value was set as 0.02. The difference of expression levels between two groups was analyzed using the T-test. It was found that two hundreds genes showed significant association (P values<$4.1\times10^{-4}$). The clustering expression of these 200 genes was further analyzed.

Quantitative Real-Time RT-PCR

Total RNA was prepared from human tissues and cultured vascular cells. Human TOR2A and preprosalusin mRNA were quantified using a LightCycler (Roche Molecular Biochemicals)-based, real-time, quantitative RT-PCR using the Master SYBR Green I kit (Shichiri et al. J. Biol. Chem. 2001 Nov. 9; 276(45):41998-2002; Shichiri et al. Cancer Res. 2002 Jan. 1; 62(1):13-7). The absolute copy number was determined using a method described before. (Matsushita et al. Br J Haematol. 2001 March; 112(4):916-26).

RNA was also isolated from PBMC or blister cells. RT Q-PCR was performed by Lightcycler using SYBR green I (Roche Applied Science). The following oligonucleotides were used:

```
granulysin:
5'-TCTCTCGTCTGAGCCC-3'             (SEQ ID NO: 6)

5'-GCAGCATTGGAAACACT-3'            (SEQ ID NO: 7)

perforin:
5'-ACCAGCAATGTGCATGTGTCTGTG-3'     (SEQ ID NO: 8)

5'-GAAGGA GGCCGTCATCTTGTGCTT-3'    (SEQ ID NO: 9)

granzyme-B:
5'-TGCAGGAAGATCGA AAGTGCG -3'     (SEQ ID NO: 10)

5'-GAGGCATGCCATTGTTTCGTC-3'       (SEQ ID NO: 11)

FasL
5'-TCATGGTTCTGGTTGCCTTG-3'        (SEQ ID NO: 12)

5'-AAATGGGCCACTTTCCTCAG-3'        (SEQ ID NO: 13)

β-actin
5'-ACATCCGCAAAGACCT-3'            (SEQ ID NO: 14)

5'-AGGG TGTAACGCAACTA-3'          (SEQ ID NO: 15)
```

SDS-PAGE and Immunoblots

Tissue or cell samples were dissolved in a reducing sample buffer (60 mM Tris HCl pH 6.8, 2% (w/v) SDS, 10% (v/v) glycerol, and 50 mM DTT) and resolved on a 15% (w/v) acryl-amide mini-gels by SDS-PAGE. Prestained molecular weight standard proteins were used to calibrate migration. Proteins in the gels were transferred for 30 minutes to a polyvinylidene difluoride (PVDF) membrane using a semi-dry transfer apparatus at 1 mA/$cm^2$ of membrane in 10 mM cyclohexylaminopropanesulfonic acid (CAPS), pH 10.4, with 10% (v/v) methanol and 0.05% (w/v) DTT. After transfer, the membrane was blocked with a blocking buffer (5% (w/v) nonfat dry milk in Tris buffered saline, pH 7.5 (TBS) with 0.1% (v/v) Tween-20 (TBST)) and subsequently incubated with rabbit antisera and peroxidase labeled goat anti-rabbit secondary antibody, both appropriately diluted in the blocking solution. After being washed with TBST, antibodies were visualized using ECL or ECL-plus (Amersham) before exposing to a film. Gels containing radiolabeled proteins were fixed, treated with Amplify (Amersham), dried, and exposed to a film at −70° C. according to the manufacturer's directions.

Granulysin ELISA

Plates (Nunc, Roskilde, Denmark) coated with RB1 mAb (50 μg/ml) were blocked with 10% FBS in a washing buffer (PBS containing 0.1% Tween-20) and serially incubated reacted at room temperature with the blocking buffer for 2 hours; 0.1 μg/ml of biotinylated RC8 mAb in the blocking buffer for 1 hour; and 0.05 U/ml of β-galactosidase-conjugated streptavidin (Roche Diagnostics) in the washing buffer. Between two incubations, the plates were washed using the washing buffer. The plates were finally incubated with 0.4 mM of 4-methylumbelliferyl-g-D-galactoside in a 10 mM sodium phosphate buffer (pH 7.0) containing 0.02% BSA, 100 mM NaCl and 1 mM MgCl2 at 37° C. for 17 hours. Then, the enzyme reaction was stopped with 100 mM glycine-NaOH (pH 10.3), and the fluorescence intensity was measured with a Cyto-Fluor 4000 fluorescence multi-well plate reader (Applied Biosystems, Foster City, Calif.) with excitation and emission wavelength of 360 nm and 460 nm, respectively.

Immunohistochemistry Staining:

Skin specimens were collected from patients with SJS/TEN, MPE or from healthy individuals. They were incubated with antibodies specifically against granulysin (RC8, MBL, Japan), granzyme B (abcam, UK), perforin (Kamiya, USA), and Fas-L (Mike-1, Alexis, Switzerland).

Expression and Purification of Recombinant Functional Granulysin

The full-length granulysin cDNA (encoding methionine1 to arginine136) was cloned into the pcDNA-TA vector (Invitrogen) to express a C-terminal $(histidine)_6$-tagged recombinant 15-kDa granulysin in *Escherichia coli* BL21 (DE3). A control vector without the full-length granulysin was used for parallel expression and purification. The recombinant proteins were expressed, and verified by Western blot. Recombinant granulysin was purified using a nickel column under denaturing conditions, and protein(s) with a molecular weight of 15 kDa were further purified from 15% SDS-PAGE gels. After purification, the proteins were reduced by the addition of 1 mM DTT, allowed to refold in the presence of oxidized DTT, and dialyzed against Tris-buffered saline. The histidine tag was then removed by thrombin treatment. The protein was quantified by Coomassie blue protein assay (Bio-Rad, Richmond, Calif.) with albumin as a standard. The concentration of total protein in the preparation showed consistently with that of granulysin when determined by ELISA. Protein purity was consistently 95%, as assessed by Coomassie staining of 15% SDS-PAGE gels. Purified Fas-L, peforin, and granzyme-B proteins were obtained from Alexis, Switzerland.

Results

Predominant Cytotoxic CD8+ T and NK Cells in the Blister Fluids of SJS/TEN

Immunophenotypes of cells present in the blister fluids from 5 patients with SJS/TEN were determined. The culprit drugs were carbamazepine (case 1, 4, and 5), phenytoin (case 2), and amoxcilline (case 5). Regardless of the culprit drugs, the majority of cells in the blister fluids were found to be CD 56+ NK cells (48% to 100%) and CD3+ T-cells with a predominance of the CD8+ (22% to 70%) subset or CD 56+ NKT cells. CD8(+)CD56(+) cells were the major subtype of the increased NKT cells in the blister cells (4% to 44%). See Table 1 below.

TABLE 1

Phenotypic analysis blister cells from patients with SJS or TEN

| | Case 1 (AdrD791) | Case 2 (AdrD811) | Case 3 (AdrD835) | Case 4 (AdrD 826) | Case 5 (AdrD 709) |
|---|---|---|---|---|---|
| Phenotype/inducing Drugs | SJS-TEN/ carbamazepine | SJS-TEN/ phenytoin | TEN/ amoxicillin | SJS-TEN/ carbamazepine | SJS/ carbamazepine |
| CD3 | 46% | 70% | 33% | 30% | 61% |
| CD4 | 8% | 0% | 0% | 8% | 0% |
| CD8 | 46% | 70% | 33% | 22% | 61% |
| CD20 | 0% | 0% | 0% | 0% | 0% |
| CD56 | 48% | 70% | 100% | 100% | 72% |
| CD3−, CD56+ (NK) | 44% | 30% | 66% | 70% | 41% |
| CD3+, CD56+ (NKT) | 4% | 44% | 33% | 22% | 31% |
| CD4+, CD56+ | 0% | 0% | 0% | 8% | 0% |
| CD8+, CD56+ (NKT) | 4% | 44% | 33% | 22% | 31% |

Cytotoxicity of Blister Cells to Autologous Target Cells

The cytotoxic activity of blister cells (effecter cells) was examined by co-culturing the blister cells (n=3) with EB virus-transformed autologous B cells as target cells (No autologous keratinocytes were available) for 4 hours, before cell apoptosis was assessed using an annexin-fluorescein isothiocyanate (FITC). It was found that, in the absence of blister cells, no cell death was detected. In contrast, with an effecter cells/target cells ratio of 5 to 1, blister cells triggered 31% of B cells apoptosis which increased slightly to 37% in the presence of a culprit drug. The results from three patients were summarized in Table 2 below.

TABLE 2

Cytotoxic activity of blister cells

| | Case 1 | Case 2 | Case 5 |
|---|---|---|---|
| Autologous B cells | 44% | 32% | 31% |
| Autologous B cells + culprit drugs | 46% | 30% | 37% |

As shown in Table 2, all blister cells displayed strong cytotoxic effect toward autologous EBV-transformed B cells. Also, adding culprit drugs did not significantly increase cytotoxicity, suggesting that these blister cells had already been activated.

Blister Fluids Induced Apoptosis and Showed Significant Cytotoxicity to Keratinocytes The toxicity of blister fluids to keratinocytes, the target skin cells in SJS/TEN, was tested by incubating the keratinocyte cells (KER-tr) in a culture medium containing 1%, 10%, or 50% of acute stage (≦3 days) blister fluids of SJS (n=4) or TEN (n=5) for 24 hours. Blister fluids from burn injuries at a concentration of 50% (n=5) were used as controls. The results were shown in Table 3 below:

TABLE 3

Cytotoxic activity of blister cells to keratinocytes

| Culture medium containing | Cell viability |
|---|---|
| 0% blister fluids | 100% |
| 1% blister fluids | ~98% |
| 10% blister fluids | ~90% |
| 50% blister fluids | ~72% |
| Control | ~98% |

As shown in Table 3, the culture media containing 50% and 10% blister fluid induced apoptosis of the keratinocyte cell line. The percentage of cell apoptosis was positively correlated with the concentration of blister fluid.

Global Gene Expression Profiles of the Blister Cells of SJS/TEN

Global gene expression profiles of blister cells from patients with SJS/TEN (n=5) were studied. The profiles were compared with the profiles of PBMC from SJS/TEN patients (n=6). PBMC was used for comparison because cells in the skin blisters were also present in the PBMC. All these patients were in active stage (within 3 days of disease onset) without any systemic medicines for treatment. Analyses for each group on U133 plus 2.0 (Affymetrix) gene chip were performed using individual RNA samples.

Two hundred differentially expressed genes were identified and statistically analyzed. Hierarchical clustering of these 200 differently expressed genes was obtained. Genes significantly up-regulated in blister cells comparing to PBMC of SJS/TEN were examined. Most of these genes were related to immune and cytotoxic T/NK cells pathway, including granulysin, granzyme B, CD3 antigen, cathepsin B, cathepsin L, and complement 1 q. Of interest, among the cytotoxic granule proteins, granulysin transcripts displayed a significant increase that was higher than those of granzyme B and porforin. The results were confirmed by real-time PCR. List below are the up-regulated genes and corresponding P values.

TABLE 4

Genes up-regulated in blister cells

| Gene name | P-value |
|---|---|
| Granulysin | 1.02E−05 |
| Granzyme B | 4.22E−05 |
| Granulysin | 5.29E−05 |
| CD3D antigen | 0.000177 |
| Cathepsin B | 0.000219 |

TABLE 4-continued

| Genes up-regulated in blister cells | |
|---|---|
| Gene name | P-value |
| Cathepsin L | 3.26E−06 |
| complement component 1, q, beta | 7.3E−06 |
| complement component 1, q, gamma | 5.32E−05 |
| adipose differentiation-related protein | 0.000219 |
| acid phosphatase 5, tartrate resistant | 0.000384 |

To verify the initial screening, real-time qPCR was carried out to measure mRNA levels of granulysin, granzyme B, perforin, and Fas/Fas in the blister cells. The levels were compared with their corresponding levels in the PBMC from SJS/TEN patients (n=13) or PBMC from normal healthy persons (n=8). It was found that the levels of granulysin mRNA in the blister cells of SJS/TEN patients were higher than those of FasL, perforin, or granzyme B. Granulysin transcript levels in the blister cells of SJS/TEN patients were 17.1 folds higher than those in the PBMC of SJS/TEN patients and 12 folds higher than those in PBMC of healthy controls. The transcript levels of granzyme B, Fas L, and perforin were also higher than those in PBMC of SJS/TEN patients and PBMC of healthy controls by 9.9 and 5.9 folds, 3.9 and 3.4 folds, and 1 and 3.2 folds, respectively. But, their increases were less so than those of granulysin.

Granulysin Protein was Highly Expressed in the Skin Lesions of SJS/TEN Patients

To further verify the mRNA results, expression of granulysin protein in the skin lesions of SJS/TEN patients were examined. Immunohistochemical analysis was carried out on skin sections from patients having SJS/TEN (n=5) or MPE (n=3). Extensive keratinocyte necrosis was found. The immunohistochemical analysis revealed intense staining of granulysin around the detached necrotic area of epidermis in SJS/TEN, but only mild positive staining in maculopapular drug eruption. In SJS/TEN samples, the expression levels of other cytotoxic proteins (perforin, granzyme B, and FasL proteins) were found to be less than that of granulysin.

Flow cytometry-double staining of blister fluid cells with anti-granulysin and anti-CD antibodies was carried out. It was found that granulysin was expressed primarily in the CD8+ and NKT cells.

High Levels of Granulysin Protein in the Blister Fluids of SJS/TEN and its Correlation with Clinical Severity Western blot was carried out to examine blister fluids of SJS/TEN for their content of granulysin. The results demonstrated that granulysin protein with a molecular weight of 15 kDa was strongly expressed in blister fluids of SJS/TEN patients. The 9 kDa form of granulysin was not detected. No granulysin was detected in the blister fluids from patients suffered from severe burn.

ELISA was performed to measure the concentrations of granulysin and other cytotoxic granule proteins in the blister fluids from SJS/TEN patients. Patients with burn injuries or bullous pemphigoid were used for controls. It was found that blister fluids of SJS/TEN patients had a high average level of granulysin: 6920.61 ng/ml (633.33 to 63392.31; n=29). In contrast, the level of granulysin was low in burn blisters (55.58 ng/ml, n=15) and blister of bullous pemphigoid (22.07 ng/ml, n=5).

The mean protein levels of granulysin in blister fluids were highest in TEN (>30% Total body surface area (TBSA) followed by SJS overlapping TEN (>10%, <29% TBSA) and SJS (<10% TBSA).

In contrast to the striking elevation of granulysin in the SJS/TEN, the protein levels of Fas ligand, perforin, and granzyme B were quite low (sFas L: 0.41 ng/ml, 0 to 2.43, n=29; perforin: 1.03 ng/ml, 0.001 to 4.16, n=29; granzyme B: 0.96 ng/ml, 0.014 to 2.36, n=29). None of them showed correlation with clinical severity.

In Vitro Cytotoxicity Test of Granulysin and Other Cytotoxic Proteins

Study was carried out to compare the potency of the cytotoxicity among various cytotoxic proteins using a keratinocyte cell line as target cells. It was found that, in vitro, recombinant 15 KD granulysin exhibited significant cytotoxicity at the level present in the SJS/TEN blister fluids (32% cell death at 4000 ng/ml). It should be noted at the concentrations present in the blister fluids of the SJS/TEN patients, only granulysin exhibited significant cytotoxicity. Fas-L, peforin, and granzyme-B did not show cytotoxicity at the levels (about 1 ng/ml) observed in the SJS/TEN blister fluids.

Direct Skin Injection of Granulysin Induced Significant Epidermal Necrosis

The in vivo effect of granulysin was evaluated by direct skin injection of purified recombinant 15 KD granulysin at a concentration of 4000 ng/ml to the skin of hair shaved mice. Injections of PBS and elutes isolated from vector only to the same mouse served as the control. After 5 times of injections within 5 hours (every 1 injection/hour), significant skin necrosis was observed at the injection site, whereas that was not observed in the site around the control injections.

The above data showed that blister fluids cells contained primarily CD 56+ and CD8+ T cells and blister fluids exhibited cytolytic activity against keratinocytes, the target skin cells in SJS/TEN. It was also showed that blister cells were cytotoxic with or without the presence of culprit drugs, suggesting these cells were already activated. This finding, however, differ from that reported in Nassif et al. J. Allergy Clin. Immunol. 2004 November; 114(5):1209-15) in that the cells as reported in Nassif et al. were cytotoxic only in the presence of drugs and the degree of toxicity observed (6-12%) was also less than the present study (30-46%).

The above results demonstrated for the first time that secretory granulysin is the key molecule responsible for the disseminated keratinocyte apoptosis and it is granulysin that underlies the missing link of the pathogenic mechanism of SJS/TEN. This is based on the striking finding of high expression levels of granulysin in the blister fluids (1000 folds) as compared with other cytotoxic proteins, granzyme B, perforin, or sFasL, which were previously implicated in the pathogenesis of SJS/TEN, and on in vitro and in vivo cytotoxicity by the granulysin at the concentration present in the blister fluids.

Previous studies on the granulysin focus on the 9 kDa mature form which is the processed form of the 15 kDa precursor (Krensky et al. Am J Transplant. 2005 August; 5(8):1789-92). Granulysin is a cationic molecule present in the granules of human cytotoxic T lymphocytes (CTLs) and natural killer cells. Similar to other cytolytic proteins, the 9-kDa granulysin is released via a calcium-dependent pathway into the intercellular space between effecter and target cells. The 9 kDa granulysin exhibits cytolytic activity against a variety of microbes and tumors (Krensky et al., Am. J. Transplant. 2005 August; 5(8):1789-92), through binding to the target cell surface based on charge, resulted in ion flux, which cause ceramide generation by activation of sphigomylinase (Gamen et al. J. Immunol. 1998 Aug. 15; 161(4): 1758-64. The ion flux also induce mitochondrial damage, the release of cytochrome C and apoptosis inducing factor, leading to programmed cell death (Pardo et al., J. Immunol. 2001

Aug. 1; 167(3):1222-9). Granulysin was also reported to be a chemoattractant and proinflammatory activator (Deng et al., J Immunol. 2005 May 1; 174(9):5243-8.)

The granulysin detected in the blister fluids in this study, however, was clearly the 15 kDa form. No 9 kDa mature form was detected despite two antibodies used in the study (polyclonal and Stanford monoclonal Ab) recognize both forms. The 15 kDa granulysin, the precursor of 9-kDa effector, has been shown to be constitutively secreted by NK and T cells via a non-granule exocytotic pathway and its levels elevated when T cells were co-cultured with target cells.

The above results showed that 15 kDa granulysin alone possessed a potent cytotoxicity. Injection of purified 15 KD granulysin at the level in blister fluids of SJS/TEN into mice skin induced significant epidermal and dermal necrosis, indicating 15 kDa granulysin is not a non-specific, un-processed products; instead, high level of extracellular secretary 15 kDa granulysin in necrotic or blistering skin of SJS/TEN may lead to extensive epidermal apoptosis/necrosis developed rapidly. This explains the frequent observation of histopathology in SJS/TEN that sparse dermal mononuclear infiltrate resulting in extensive epidermal necrosis (Quinn et al., Arch Dermatol. 2005 June; 141(6):683-7).

The levels of granulysin in the blister fluids correlated well with the clinical severity. TEN, which has the most extensive skin involvement (>30% total body surface area), has the highest levels of granulysin, followed by overlapping SJS/TEN and SJS. This suggested that granulysin may be used to monitor the disease progression and used as a target to develop novel therapeutics for these life-threatening conditions which still carry high mobidity and mortality. In addition, the findings showed that granulysin was elevated only in SJS/TEN, and not other bullous skin diseases, such as bullous pemphigoid, suggested that measurement of granulysin is helpful in differential diagnosis of bullous skin diseases thus avoiding the skin biopsy.

The significance of the above study goes beyond the SJS/TEN. First, GVHD has skin and other internal organ manifestations resemble those in SJS/TEN. It was found that granulysin was also highly expressed in the gut, liver, and skin of GVHD. Second, the current emphasize of perforin/granzyme as the main pathway of the granule-mediated cell death should be revisited in view of the results described herein. Furthermore, results described herein challenge the current view that T cell-mediated killing of the target cells requires direct contact between NK/CTL-cells and target cells.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A method of treating a granulysin-mediated autoimmune disorder in a subject, the method comprising administering to a subject in need thereof an effective amount of a granulysin inhibitor, the granulysin-mediated autoimmune disorder being Steven-Johnson syndrome (SJS), toxic epidermal necrolysis (TEN), or graft-versus-host disease (GVHD), wherein the granulysin inhibitor is an antibody that specifically binds to a granulysin consisting of the amino acid sequence of SEQ ID NO:3.

2. The method of claim 1, wherein the antibody is a monoclonal antibody.

3. The method of claim 1, wherein the granulysin-mediated autoimmune disorder is SJS.

4. The method of claim 1, wherein the granulysin-mediated autoimmune disorder is TEN.

5. The method of claim 1, wherein the granulysin-mediated autoimmune disorder is GVHD.

* * * * *

```
                           SEQUENCE LISTING


<160> NUMBER OF SEQ ID NOS: 15

<210> SEQ ID NO 1
<211> LENGTH: 83
<212> TYPE: PRT
<213> ORGANISM: Homo sapiens

<400> SEQUENCE: 1

Gly Arg Asp Tyr Arg Thr Cys Leu Thr Ile Val Gln Lys Leu Lys Lys
  1               5                  10                  15

Met Val Asp Lys Pro Thr Gln Arg Ser Val Ser Asn Ala Ala Thr Arg
             20                  25                  30

Val Cys Arg Thr Gly Arg Ser Arg Trp Arg Asp Val Cys Arg Asn Phe
         35                  40                  45

Met Arg Arg Tyr Gln Ser Arg Val Thr Gln Gly Leu Val Ala Gly Glu
     50                  55                  60

Thr Ala Gln Gln Ile Cys Glu Asp Leu Arg Leu Cys Ile Pro Ser Thr
 65                  70                  75                  80

Gly Pro Leu


<210> SEQ ID NO 2
<211> LENGTH: 252
<212> TYPE: DNA
<213> ORGANISM: Homo sapiens

<400> SEQUENCE: 2

ggccgtgact acaggacctg tctgacgata gtccaaaaac tgaagaagat ggtggataag      60

cccacccaga gaagtgtttc caatgctgcg acccgggtgt gtaggacggg gaggtcacga     120
```

-continued

```
tggcgcgacg tctgcagaaa tttcatgagg aggtatcagt ctagagttac ccagggcctc    180

gtggccggag aaactgccca gcagatctgt gaggacctca ggttgtgtat accttctaca    240

ggtcccctct ga                                                        252


<210> SEQ ID NO 3
<211> LENGTH: 145
<212> TYPE: PRT
<213> ORGANISM: Homo sapiens

<400> SEQUENCE: 3

Met Ala Thr Trp Ala Leu Leu Leu Leu Ala Ala Met Leu Leu Gly Asn
  1               5                  10                  15

Pro Gly Leu Val Phe Ser Arg Leu Ser Pro Glu Tyr Tyr Asp Leu Ala
             20                  25                  30

Arg Ala His Leu Arg Asp Glu Glu Lys Ser Cys Pro Cys Leu Ala Gln
         35                  40                  45

Glu Gly Pro Gln Gly Asp Leu Leu Thr Lys Thr Gln Glu Leu Gly Arg
     50                  55                  60

Asp Tyr Arg Thr Cys Leu Thr Ile Val Gln Lys Leu Lys Lys Met Val
 65                  70                  75                  80

Asp Lys Pro Thr Gln Arg Ser Val Ser Asn Ala Ala Thr Arg Val Cys
                 85                  90                  95

Arg Thr Gly Arg Ser Arg Trp Arg Asp Val Cys Arg Asn Phe Met Arg
            100                 105                 110

Arg Tyr Gln Ser Arg Val Thr Gln Gly Leu Val Ala Gly Glu Thr Ala
        115                 120                 125

Gln Gln Ile Cys Glu Asp Leu Arg Leu Cys Ile Pro Ser Thr Gly Pro
    130                 135                 140

Leu
145


<210> SEQ ID NO 4
<211> LENGTH: 438
<212> TYPE: DNA
<213> ORGANISM: Homo sapiens

<400> SEQUENCE: 4

atggctacct gggccctcct gctccttgca gccatgctcc tgggcaaccc aggtctggtc     60

ttctctcgtc tgagccctga gtactacgac ctggcaagag cccacctgcg tgatgaggag    120

aaatcctgcc cgtgcctggc ccaggagggc ccccagggtg acctgttgac caaaacacag    180

gagctgggcc gtgactacag gacctgtctg acgatagtcc aaaaactgaa gaagatggtg    240

gataagccca cccagagaag tgtttccaat gctgcgaccc gggtgtgtag gacggggagg    300

tcacgatggc gcgacgtctg cagaaatttc atgaggaggt atcagtctag agttacccag    360

ggcctcgtgg ccggagaaac tgcccagcag atctgtgagg acctcaggtt gtgtatacct    420

tctacaggtc ccctctga                                                  438


<210> SEQ ID NO 5
<211> LENGTH: 62
<212> TYPE: PRT
<213> ORGANISM: Homo sapiens
```

<400> SEQUENCE: 5

Met Ala Thr Trp Ala Leu Leu Leu Leu Ala Ala Met Leu Leu Gly Asn
1 5 10 15

Pro Gly Leu Val Phe Ser Arg Leu Ser Pro Glu Tyr Tyr Asp Leu Ala
20 25 30

Arg Ala His Leu Arg Asp Glu Glu Lys Ser Cys Pro Cys Leu Ala Gln
35 40 45

Glu Gly Pro Gln Gly Asp Leu Leu Thr Lys Thr Gln Glu Leu
50 55 60

<210> SEQ ID NO 6
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 6
tctctcgtct gagccc 16

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 7
gcagcattgg aaacact 17

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 8
accagcaatg tgcatgtgtc tgtg 24

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 9
gaaggaggcc gtcatcttgt gctt 24

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 10
tgcaggaaga tcgaaagtgc g 21

-continued

```
<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11

gaggcatgcc attgtttcgt c                                              21


<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12

tcatggttct ggttgccttg                                                20


<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13

aaatgggcca ctttcctcag                                                20


<210> SEQ ID NO 14
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14

acatccgcaa agacct                                                    16


<210> SEQ ID NO 15
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15

agggtgtaac gcaacta                                                   17
```